United States Patent [19]
Fleischer et al.

[11] Patent Number: 5,741,611
[45] Date of Patent: Apr. 21, 1998

[54] METHOD OF PREPARING AN ELECTROCHEMICAL SYSTEM OPERATED AT AMBIENT TEMPERATURES

[75] Inventors: Niles A. Fleischer; Joost Manassen, both of Rehovot; Steve Daren, Nes Ziona, all of Israel

[73] Assignee: E.C.R. - Electro-Chemical Research Ltd., Yavne, Israel

[21] Appl. No.: 805,414

[22] Filed: Feb. 26, 1997

Related U.S. Application Data

[62] Division of Ser. No. 697,835, Aug. 28, 1996, Pat. No. 5,643,689.

[51] Int. Cl.$^6$ ........................................................ H01M 6/18
[52] U.S. Cl. .......................... 429/192; 427/115; 29/623.5
[58] Field of Search .............................. 29/623.1, 623.5; 427/115; 252/62.2; 204/421, 296; 429/33, 192

[56] References Cited

U.S. PATENT DOCUMENTS

| | | |
|---|---|---|
| 3,265,536 | 8/1966 | Miller et al. . |
| 4,024,036 | 5/1977 | Nakamura et al. . |
| 4,089,816 | 5/1978 | Sano et al. . |
| 4,179,491 | 12/1979 | Howe et al. . |
| 4,306,774 | 12/1981 | Nicholson . |
| 4,380,575 | 4/1983 | Nakamura et al. . |
| 4,594,297 | 6/1986 | Polak et al. . |
| 4,664,761 | 5/1987 | Zupancic et al. . |
| 5,272,017 | 12/1993 | Swathirajan et al. . |

OTHER PUBLICATIONS

Lundsgaard, J.S. et al "A Novel Hydrogen Gas Sensor Based on Hydrogen Uranyl Phosphate", Solid State Ionics, 7 (1982) 53–65 no month.

Kordesch, K.V., "25 Years of Fuel cell Development (1951–1976)", J. Electrochemical Society, pp. 77c–91c (Mar., 1978).

Fein et al, "Evaluation of Transthoracic Electrical Impedance in the Diagnosis of Pulmonary Edema" *Circulation*, vol. 60, No. 5, pp. 1156–1160 (1979) no month.

Berman et al, "Transthoracic Electrical Impedance as a Guide to Intravascular Overload", *Arch. Surg.*, vol. 102, pp. 61–64 (1971) no month.

Luepker et al, "Transthoracic electrical impedance: Quantitative evaluation of a non-invasive measure of thoracic fluid volume", *American Heart Journal*, vol. 85, No. 1, pp. 83–93, (1973) no month.

Staub, N., "Clinical Use of Lung Water Measurements", *Chest*, vol. 90, No. 4, pp. 588–594, (1986) no month.

Staub et al, "Conference report of a workshop on the measurement of lung water", *Critical Care Medicine*, vol. 8, No. 12, pp. 752–759 (1980) no month.

Miniati et al, "Detection of lung edema", *Critical Care Medicine*, vol. 15, No. 12, pp. 1146–1155 (1987) no month.

*Primary Examiner*—Anthony Skapars
*Attorney, Agent, or Firm*—Mark M. Friedman

[57] ABSTRACT

A non-liquid proton conductor membrane for use in an electrochemical system, under ambient conditions, the electrochemical system comprising (a) an anode plate; (b) a cathode plate; and (c) a non-liquid proton conductor membrane interposed between the anode plate and cathode plate, such that an electrical contact is formed between the anode plate and cathode plate via the non-liquid proton conductor membrane and ions flow therebetween, the non-liquid proton conductor membrane including (i) a matrix polymer dissolvable in a first solvent; (ii) an acidic multimer dissolvable in the first solvent; wherein, the matrix polymer is selected such that when the non-liquid proton conductor membrane is contacted with a second solvent, the non-liquid proton conductor membrane swells and as a result the electrical contact improves.

2 Claims, 3 Drawing Sheets

10

20

METHOD OF PREPARING AN ELECTROCHEMICAL SYSTEM OPERATED AT AMBIENT TEMPERATURES

This is a divisional application of U.S. patent application Ser. No. 08/697,835, filed Aug. 28, 1996 now U.S. Pat. No. 5,643,689.

FIELD AND BACKGROUND OF THE INVENTION

The present invention relates to electrochemical systems. More particularly, the present invention relates to non-liquid proton conductors such as solid polymer proton conducting membranes, for use in electrochemical systems, under ambient conditions.

An electrochemical system includes two electrodes, referred to as cathode, where reduction occurs during use, and anode, where oxidation occurs. When electrons flow through an electrical circuit from one electrode to the other, i.e., according to the above definitions from the anode to the cathode, charge is equalized by movement of ions from one electrode to the other via the electrolyte.

To this end, in most electrochemical systems the electrodes are separated therebetween by an aqueous solution, referred to as an electrolyte, through which ions can freely move.

However, as it is not always convenient to have a liquid present in an electrochemical system, systems were developed, wherein a non-liquid electrolyte is employed for proton conduction. For proton conduction, non-liquid electrolytes are non-liquid proton conductors typically in the form of an organic polymer or an inorganic material. For various uses of non-liquid electrolytes in electrochemical systems the reader is referred to U.S. Pat. Nos. 3,265,536 to Miller et al., 4,664,761 to Zupancic et al., 5,272,017 to Swathirajan et al., 4,594,297 to Polak et al., 4,380,575 to Nakamura et al., 4,024,036 to Nakamura et al., 4,089,816 to Sano et al., 4,306,774 to Nicholson, and 4,179,491 to Howe et al., Since electrochemical processes are advantageously run at elevated temperatures, and as heat can be produced during the electrochemical process, these non-liquid electrolytes have to be heat resistant.

Nevertheless, there are many electrochemical applications which are run at room temperature, i.e., ambient temperature, and due to size or current use, do not produce much heat.

For use at elevated temperatures up to one hundred °C., a familiar organic material is a Du-Pont product under the name of Nafion, which contains fluorinated methanesulfonic acid groups giving it its thermal stability. An example of an inorganic material frequently used in this range of temperatures is hydrogenuranylphosphate.

However, for ambient conditions these materials are not very convenient, as they are very expensive and do not excel in ionic conductivity at room temperatures. Therefore, their activity is boosted by working at higher temperatures and pressures, where currents per unity of area are maximized and as a result, less area of the expensive membrane is necessary. For use under ambient conditions, commercially available organic polymer ion exchange sheets are typically employed as non-liquid electrolytes. These however are expensive, unstable and have the additional disadvantage of a bad electrical contact with the electrodes, which at ambient temperatures is more of a hindrance than at elevated temperatures.

In order to evade these problems, use of heterogeneous systems, where an insoluble ion exchange material is mixed with a polymer, or alternatively, use of homogeneous systems, where acids like sulfuric, phosphoric or heteropolyacids are dissolved in a polymer were initiated. Nevertheless, the former still have the disadvantage of bad electrical contact with the electrodes, while in the latter, the acidic material tends to leach out.

There is thus a widely recognized need for, and it would be highly advantageous to have, a non-liquid proton conductor for use in electrochemical systems under ambient conditions, which systems are characterized by (i) an electrical contact between the non-liquid proton conductor and the electrodes, which is as good as that obtained using liquid electrolytes; and (ii) a proton conductor which by nature does not leach out.

SUMMARY OF THE INVENTION

According to the present invention there is provided a non-liquid proton conductor membrane for use in electrochemical systems under ambient conditions.

According to further features in preferred embodiments of the invention described below, the electrochemical system comprising (a) an anode plate; (b) a cathode plate; and (c) a non-liquid proton conductor membrane interposed between the anode plate and cathode plate, such that an electrical contact is formed between the anode plate and the cathode plate via the non-liquid proton conductor membrane and ions flow therebetween, the non-liquid proton conductor membrane including (i) a matrix polymer dissolvable in a first solvent; (ii) an acidic multimer dissolvable in the first solvent; wherein, the matrix polymer is selected such that when the non-liquid proton conductor membrane is contacted with a second solvent, the non-liquid proton conductor membrane swells and as a result the electrical contact between the anode plate and/or the cathode plate and the membrane, improves.

According to still further features in the described preferred embodiments the first and second solvents are water.

According to still further features in the described preferred embodiments the second solvent is externally added to the system.

According to still further features in the described preferred embodiments the electrochemical system is a fuel cell and the second solvent is water formed while the cell operates.

According to still further features in the described preferred embodiments the matrix polymer is selected from the group consisting of polyvinylidene fluoride, polyhydroxyethylene, polyethyleneimine, polyacrylic acid, polyethylene oxide, poly-2-ethyl-2-oxazoline, phenol formaldehyde resins, polyacrylamide, poly-N-substituted acrylamide, poly-4-vinylpyridine, polymethacrylic acid, poly-N-vinylimidazole, polyvinyl sulfonic acid, poly-2-vinylpyridine, polyvinylpyrrolidone, polyvinylphosphonic acid, a polymer having a hydrophilic functional moiety, agar, agarose, polyvinyl alcohol and mixtures thereof.

According to still further features in the described preferred embodiments the acidic multimer is obtained by acidification of an organic multimer.

According to still further features in the described preferred embodiments the organic multimer is selected from the group consisting of polyolefins, polystyrenes, phthalocyanines, porphyrins, nylons, paraffin wax and a vinyl polymer or copolymer having a functional group of the formula $[-CH_2-]_n$.

According to still further features in the described preferred embodiments the acidic multimer is obtained by polymerization or copolymerization of monomers.

According to still further features in the described preferred embodiments the acidic multimer is in its salt forth during the preparation of said membrane.

According to still further features in the described preferred embodiments the acidic multimer is selected from the group consisting of sulfonated wax, polyvinylsulfonic acid, polyvinylphosphoric acid, sulfonated polyolefins, sulfonated polystyrenes, sulfonated phthalocyanines, sulfonated porphyrins, poly-2-acrylamido-2-methylpropanesulfonic acid, polyacrylic acid and polymethacrylic acid.

According to still further features in the described preferred embodiments the system is a fuel cell, the anode plate and the cathode plate contain a catalyst selected from the group consisting of platinum, palladium, rhodium, ruthenium, tin, cobalt, chromium, metal phthalocyanines, metaloporphyrins and mixtures thereof.

According to still further features in the described preferred embodiments the system is a battery, the anode plate includes a mixture of a first ingredient selected from the group consisting of chloranilic acid and compounds (e.g., salts and oxides) containing metal ions having a redox potential ranging between −400 to +400 mvolts versus a standard hydrogen electrode and of a second ingredient selected from the group consisting of acetylene black, forms of carbon like carbon black and activated carbon, and the cathode plate includes a mixture of a third ingredient selected from the group consisting of compounds (e.g., salts, oxides, sulfates such as manganese sulfate) containing metal ions having a redox potential higher than one volt versus the standard hydrogen electrode and a fourth ingredient selected from the group consisting of acetylene black, forms of carbon like carbon black and activated carbon.

According to still further features in the described preferred embodiments the system is selected from the group consisting of batteries, fuel cells, capacitors and electrolizers.

According to still further features in the described preferred embodiments the non-liquid proton conductor membrane further includes a filler.

According to still further features in the described preferred embodiments the filler is selected from the group consisting of alumina powder, titania powder, silica powder, ceria powder, polyolefin powder, polystyrene powder and their acidified derivatives.

According to still further features in the described preferred embodiments the non-liquid proton conductor membrane further includes cross-links formed at least between molecules of the matrix polymer.

According to still further features in the described preferred embodiments the non-liquid proton conductor membrane further includes cross-links formed at least between molecules of the acidic multimer.

According to still further features in the described preferred embodiments the non-liquid proton conductor membrane further includes cross-links formed at least between molecules of the acidic multimer and molecules of the matrix polymer.

According to still further features in the described preferred embodiments provided is a method of preparing a non-liquid proton conductor membrane for use in electrochemical systems as described hereinabove and further described below, the method comprising the steps of (a) dissolving a matrix polymer and an acidic multimer in a first solvent to obtain a homogenous solution; (b) pouring the homogenous solution onto a surface; and (c) evaporating the first solvent to obtain the non-liquid proton conductor membrane.

According to still further features in the described preferred embodiments provided is a method of preparing an electrochemical system such as batteries, a fuel cell, a capacitor and an electrolizer, operated at ambient temperatures, the method comprising the steps of (a) dissolving a matrix polymer and an acidic multimer in a first solvent to obtain a homogenous solution; (b) pouring the homogenous solution onto a surface; (c) evaporating the first solvent and therefore obtaining a non-liquid proton conductor membrane; and (d) interposing the non-liquid proton conductor membrane in an electrical contact between an anode plate and a cathode plate. The matrix polymer is selected such that when the non-liquid proton conductor membrane is contacted with a second solvent, the non-liquid proton conductor membrane swells and as a result the electrical contact improves.

According to still further features in the described preferred embodiments the methods further comprising the step of forming cross-links within the non-liquid proton conductor membrane.

According to still further features in the described preferred embodiments provided is a reference electrode for reference measurements of non-liquid systems, the reference electrode comprising an electrode embedded in a non-liquid proton conductor material, such that an electrical contact is formed between the electrode and the non-liquid proton conductor material, the non-liquid proton conductor material including (i) a matrix polymer dissolvable in a first solvent; and (ii) an acidic multimer dissolvable in the first solvent; wherein, the matrix polymer is selected such that when the non-liquid proton conductor material is contacted with a second solvent, the non-liquid proton conductor material swells and as a result the electrical contact improves.

The present invention successfully addresses the shortcomings of the presently known configurations by providing a non-liquid proton conductor membrane for use in electrochemical systems under ambient conditions, the conductors according to the invention are characterized by (i) an electrical contact which is as good as that obtained with liquid electrolytes; and by (ii) being leach proof.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of non-liquid proton conductor membranes i.e., solid polymer proton conducting substrates, for use in electrochemical systems under ambient conditions. Specifically, the present invention can be used (i) to improve the electrical contact between the non-liquid proton conductor membrane and the electrodes of the electrochemical system to obtain conductivity which is as good as that obtained with liquid electrolytes; and (ii) to provide an electrochemical system having a proton conductor which by nature does not leach out.

The principles and operation of a non-liquid proton conductor membranes according to the present invention may be better understood with reference to the drawings and accompanying descriptions.

Figure 1:
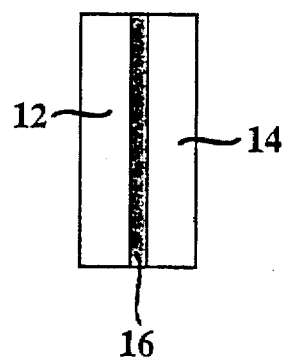
FIG. 1 is a schematic depiction of an electrochemical system according to the present invention.

Referring now to the drawings, FIG. 1 illustrates few of the basic components of an electrochemical system according to the present invention, generally referred to hereinbelow as system 10.

System 10 includes an anode plate 12, a cathode plate 14 and a non-liquid proton conductor membrane 16 interposed between anode plate 12 and cathode plate 14, such that an electrical contact is formed between anode plate 12 and cathode plate 14 via non-liquid proton conductor membrane 16 and ions flow therebetween.

According to the present invention, non-liquid proton conductor membrane 16 includes a matrix polymer dissolvable in a first solvent and an acidic multimer (i.e., polymer and/or oligomer) also dissolvable in the first solvent, such that both materials may be homogeneously dissolved in their multimeric forms in the first solvent, which is preferably water, and thereafter dried out to obtain non-liquid proton conductor membrane 16.

Further according to the present invention, the matrix polymer is selected such that when non-liquid proton conductor membrane 16 is contacted with a second solvent, typically water, non-liquid proton conductor membrane 16 swells, and as a result the electrical contact between anode plate 12 and cathode plate 14 formed via non-liquid proton conductor membrane 16, improves.

Selecting acidic multimer which can be homogeneously mixed with the matrix polymer ensures that (i) the acidic multimer which is the proton conducting agent in the system, is uniformly distributed within non-liquid proton conductor membrane 16; and (ii) at the same time the acidic multimer by nature cannot leach out of the membrane, as it is homogeneously distributed among the matrix polymer molecules.

Electrochemical systems according to the present invention may be batteries, fuel cells, capacitors, electrolizers and reference electrodes used in these systems.

In batteries the electrodes (i.e., cathode and anode) contain a material which is capable of redox reactions. The difference between the redox potential of the anode and the cathode gives the open circuit potential of the battery. When the electrodes are connected over a load, a current starts to flow. In order not to lose valuable energy, it is preferred that the voltage changes as little as possible when the current starts to flow. In this respect the resistance of the electrolyte becomes important. If the electrolyte is a good proton conductor, appreciable currents can be drawn without a drop in voltage. When the redox reactions of the electrode are reversible, the battery is rechargeable. When, on the other hand, the redox reactions of the electrode are irreversible, the battery is a primary battery, which can be used only once. Further details concerning the construction and operation of batteries may be found in "Handbook of Batteries", second edition, editor in chief David Linden. McGraw Hill, N.Y., 1994, which is incorporated by reference as if fully set forth herein.

The resistance of the battery depends not only on the proton conductivity of the electrolyte but also on the contact between the electrolyte and electrodes. If the electrolyte is a liquid, there is an inherent good contact. Yet, if the electrolyte is a rigid polymer, contact may become be poor. By using a swellable matrix polymer, the physical and thus electrical contact is tremendously improved, as the non-liquid proton conductor membrane adapts itself to the roughness of the electrode surfaces as a liquid would.

Fuel cells are actually batteries where the redox materials are constantly fed into the system, all as well known in the art. In fuel cells, an electrolyte is positioned and on both sides of which a catalyst is deposited. Hydrogen is fed towards the anode plate and oxygen towards the cathode plate. Because of the catalyst, oxygen is reduced and hydrogen is oxidized to a proton which passes through the electrolyte where it combines with the reduced oxygen to form water. Therefore in a hydrogen/oxygen fuel cell water is produced during operation.

Dependent on the working temperature, many kinds of electrolytes are currently used in fuel cells. For ambient conditions non-liquid electrolytes are attractive. As water is produced during the operation of the fuel cell, a non-liquid proton conductor membrane which includes a water swellable polymer will swell and make a superior contact with the catalyst layers. The theoretical voltage of a fuel cell is 1.23 volts but in practice mostly not more than 1 volt is obtained. Further details concerning the construction and operation of fuel cells may be found in "Fuel Cell Systems", edited by Leo J. M. J. Blomen and Michael M. Mugerwa, Plenum N.Y. and London, which is incorporated by reference as if fully set forth herein.

The opposite of a fuel cell is an electrolizer. By applying a voltage and passing water alongside the catalysts, hydrogen and oxygen are evolved. Further details concerning the construction and operation of electrolizers may be found in "Fuel Cell Systems", edited by Leo J. M. J. Blomen and Michael M. Mugerwa, Plenum N.Y. and London, 1993, which is incorporated by reference as if fully set forth herein.

Many reference electrodes contain a liquid and are therefore difficult to use in non-liquid systems. It is possible to use the non-liquid proton conductor material according to the invention also for making a reference electrode for non-liquid systems. To this end, a reference electrode is made for instance from silver/silver chloride embedded in agar/agar. This system is immersed in a polymer solution containing a multimeric acid, taken out and given to dry. There is now a non-liquid proton conducting barrier between the system to be measured and the reference electrode, which prevents leaching out of the active materials. Further details concerning the construction and operation of reference electrodes may found in "Reference Electrodes Theory and Practice", George J. Janz and David J. Ives editors, Academic Press. New York and London, 1961, which is incorporated by reference as if fully set forth herein.

Figure 2:
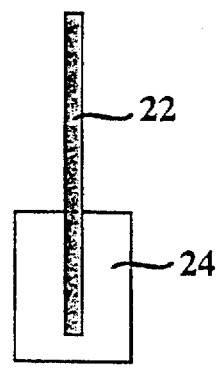
FIG. 2 is a schematic depiction of a reference electrode according to the present invention.

With reference now to FIG. 2, according to the invention, provided is a reference electrode, generally referred to hereinbelow as reference electrode 20 which is suitable for reference measurements of non-liquid systems.

Reference electrode 20 includes an electrode 22 embedded in a non-liquid proton conductor material 24, such that an electrical contact is formed between electrode 22 and non-liquid proton conductor material 24. Non-liquid proton conductor material includes a matrix polymer dissolvable in a first solvent; and an acidic multimer also dissolvable in the first solvent. The matrix polymer is selected such that when non-liquid proton conductor material 24 is contacted with a second solvent it swells and as a result the electrical contact improves.

According to preferred embodiments of the invention the second solvent (e.g., water or aqueous solution) is added to the system to swell the non-liquid proton conductor membrane. This is the case in systems such as batteries, capacitors, electrolizers and reference electrodes.

According to other preferred embodiments of the invention the water is formed while the electrochemical system operates. This is the case in fuel cells where water is formed during the reduction of oxygen.

The matrix polymer may be of any type which will swell when contacted with a selected solvent (e.g., water). Examples include but are not limited to polyvinylidene fluoride, polyhydroxyethylene, polyethyleneimine, polyacrylic acid, polyethylene oxide, poly-2-ethyl-2-oxazoline, phenol formaldehyde resins, polyacrylamide, poly-N-substituted acrylamide, poly-4-vinylpyridine, polymethacrylic acid, poly-N-vinylimidazole, polyvinyl sulfonic acid, poly-2-vinylpyridine, polyvinylpyrrolidone, polyvinylphosphonic acid, a polymer having a hydrophilic functional moiety, agar, agarose, polyvinyl alcohol and mixtures thereof.

The acidic multimer may be obtained by acidification of an organic multimer, such as but not limited to polyolefins, polystyrenes, phthalocyanines, porphyrins, nylons, paraffin wax and a vinyl polymer or copolymer having a functional group of the formula $[-CH_2-]_n$.

Alternatively, the acidic multimer is obtained by polymerization or copolymerization of suitable monomers such as but not limited to vinyl sulfonic acid, vinyl phosphoric acid, acrylic acid, methacrylic acid, 2-acrylamido-2-methylpropylsulfonic acid, styrenesulfonic acid and other vinylmonomers carrying an acidic group, which can be polymerized or copolymerized in the presence or absence of other vinyl including monomers.

In both cases the acidic multimer may be in its salt form during the preparation of said membrane, or its hydrogen containing form.

In preferred embodiments the acidic multimer is sulfonated wax, polyvinylsulfonic acid, polyvinylphosphoric acid, sulfonated polyolefins, sulfonated polystyrenes, sulfonated phthalocyanines, sulfonated porphyrins, poly-2-acrylamido-2-methylpropanesulfonic acid, polyacrylic acid or polymethacrylic acid, yet other acidic polymers are also suitable.

When the electrochemical system is a fuel cell, the anode plate and cathode plate may contain a catalyst such as but not limited to platinum, palladium, rhodium, ruthenium, tin, cobalt, chromium, metal phthalocyanines, metaloporphyrins and mixtures thereof.

When the electrochemical system is a battery, the anode plate includes a mixture of a first ingredient such as but not limited to chloranilic acid and compounds (e.g., salts and oxides) containing metal ions having a redox potential ranging between −400 to +400 mvolts versus a standard hydrogen electrode, and of a second ingredient such as but not limited to acetylene black, forms of carbon like carbon black and activated carbon. The cathode plate includes a mixture of a third ingredient such as but not limited to compounds (e.g., salts, oxides and sulfates such as manganese sulfate) containing metal ions having a redox potential higher than one volt versus the standard hydrogen electrode, and a fourth ingredient such as but not limited to acetylene black, forms of carbon like carbon black and activated carbon.

In some preferred embodiments the non-liquid proton conductor membrane further includes a filler, such as but not limited to alumina powder, titania powder, silica powder, ceria powder, polyolefin powder, polystyrene powder and their acidified derivatives.

According to the invention there is also provided a method of preparing a non-liquid proton conductor membrane for use in electrochemical systems, which method includes the steps of (a) dissolving a matrix polymer and an acidic multimer in a first solvent to obtain a homogenous solution; (b) pouring the homogenous solution onto a surface; and (c) evaporating the first solvent to obtain the non-liquid proton conductor membrane.

According to the invention there is further provided a method of preparing an electrochemical system such as batteries, fuel cells, capacitors and electrolizers, operated at ambient temperatures, which method includes the steps of (a) dissolving a matrix polymer and an acidic multimer in a first solvent to obtain a homogenous solution; (b) pouring the homogenous solution onto a surface; (c) evaporating the first solvent and therefore obtaining a non-liquid proton conductor membrane; and (d) interposing the non-liquid proton conductor membrane in an electrical contact between an anode plate and a cathode plate. The matrix polymer is selected such that when the non-liquid proton conductor membrane is contacted with a second solvent, the non-liquid proton conductor membrane swells and as a result the electrical contact improves.

In a preferred embodiment, any of the methods further includes a step of forming cross-links within the non-liquid proton conductor membrane and/or including a filler within the membrane. The cross-links and/or filler are directed at providing the membrane with physical toughness, which is important in some applications. This may permit the use of thinner membranes which thereby improve the conductivity of the electrolytic layer.

Reference is now made to the following examples, which together with the above descriptions, illustrate the invention.

EXAMPLE 1

Preparation of a non-liquid proton conductor membrane

A general scheme is herein described for the preparation of a non-liquid proton conductor membrane according to the invention.

First, a matrix polymer solution is prepared, mostly of the order of 5–10% polymer, typically in water; yet other solvents, e.g., acetone, acetonitrile, alcohol, methylethylketone, dioxane, tetrahydrofuran, dimethylformamide, dimethylsulfoxide and the like are also suitable depending on the nature of the matrix polymer and the multimeric acid, see stage 2 below.

Second, an oligomeric or polymeric (i.e., multimeric) acid, i.e., acidic multimer, is prepared either by polymerization or copolymerization of monomers, or by treatment of an existing polymer or oligomer by which acidic groups are introduced thereon. The acidic multimer thus formed, as such, or in the form of one of its salts, is dissolved in the same solvent as used to dissolve the matrix polymer.

Third, both solutions are mixed carefully taking care that the mixture stays a clear homogenous solution.

Fourth, if the mixture contains a salt form of the multimeric acid, it can be treated with the hydrogen form of a strongly acidic ion exchange resin (e.g., Dowex or Amberlite beads), which may be filtered off or left in the mixture. This results in replacement of the metal ions by protons.

Fifth, a filler such as but not limited to alumina powder, titania powder, silica powder, ceria powder, polyolefin powder, polystyrene powder and their acidified derivatives, or beads (e.g., the resin beads) can be added. The filler increases the toughness of the membrane. Ion exchange resin left in the mixture as described under the fourth stage above may serve also the function of a filler.

And, finally, the mixture thus obtained is poured onto a surface and the solvent given to evaporate.

For some embodiments, the physical toughness of the membrane is of great importance. In order to increase the toughness of the membrane, a cross linking procedure may be employed. To this end, either a cross-linking substance is added to the solution prior to the final step, wherein the solvent is evaporated, or, a cross linking treatment such as heat and/or radiation is applied to the membrane post the final stage. In preferred embodiments, cross-links are formed at least between molecules of the matrix polymer, at least between molecules of the acidic multimer, or at least between molecules of the acidic multimer and molecules of the matrix polymer.

EXAMPLE 2

Preparation of a fuel cell

Soft paraffin wax is dissolved in carbon tetrachloride and a quantity of chlorosulfonic acid is added in an amount sufficient for reaching a sulfonation product of 3 meq/gram. The mixture is boiled for two hours, afterwhich time an insoluble layer is formed. The solvent containing unreacted wax is decanted. After washing and drying the residue, a blackish water soluble product is obtained. This product is dissolved in a 5% polyvinyl alcohol (PVA) in water solution, such that the ratio of sulfonated wax to PVA is 1 to 10. The obtained solution is poured on a flat surface and given to dry to obtain a non-liquid proton conductor membrane.

Fuel cell electrodes of the E-Tek Inc. (6 Mercer Road, Natick, Mass. 01760 USA), containing 1 mg platinum (Pt) catalyst per one $cm^2$ are wetted with a 50% phosphoric acid solution in alcohol and the alcohol removed by drying at 80° C. In such a way the pores characterizing the surface of the fuel cell electrodes are partially filled with phosphoric acid. This procedure is necessary to get ionic conduction also within the pores where the polymer does not enter during preparation.

The non-liquid proton conductor membrane obtained above is wetted slightly with 2M phosphoric acid in order to make it sticky, and the treated electrodes are pressed on, by which contact is made between the phosphoric acid within the pores and the membrane.

Using hydrogen as the fuel and oxygen as the oxidant, the fuel cell thus prepared has an open circuit voltage of 993 mV, and a current of 900 $mA/cm^2$ can be maintained at a voltage of 102 mV. At 200 $mA/cm^2$ the voltage is 533 mV. All data were derived under ambient conditions.

EXAMPLE 3

Preparation of a battery

A solution of 20 grams of polyvinyl alcohol (PVA) in 500 ml water is prepared. To 15 ml of the obtained solution, 0.6 grams of a 25% aqueous solution of polyvinylsulfonic acid sodium salt is added, as well as 1 gram of Dowex 50 W×8 200-400 mesh strongly acidic ion exchanger. After stirring, the solution is poured onto a flat surface and given to dry.

The resulting non-liquid proton conductor membrane which contains the Dowex particles is interposed between two electrodes, wherein the anode plate is a mixture of chloranilic acid and acetylene black and the cathode plate a mixture of manganese sulfate and acetylene black, both slightly wetted with 4M sulfuric acid.

This cell cycles between 0.8 and 2.0 volts at 4 mA per $cm^2$, and is capable of cycling for hundreds of cycles giving an energy density of approximately 40 $mWh/cm^3$. All data were derived under ambient conditions.

EXAMPLE 4

Preparation of a reference electrode

A silver wire is thoroughly anodized in a chloride containing solution in the dark. The resulting silver/silver chloride system is covered with an agar/agar layer containing chloride. After drying, it is immersed in a solution prepared as described under Example 2 above and dried. The resulting reference electrode has a potential of 210 mV towards a standard hydrogen electrode and can be advantageously used as a reference electrode in non liquid systems. All data were derived under ambient conditions.

EXAMPLE 5

Preparation of a fuel cell

A solution of 20 grams of polyvinylalcohol in 500 ml of water is prepared. To 30 ml of this solution, 0.5 gram of a 25% aqueous solution of polyvinylsulfonic acid sodium salt is carefully added. When the mixture is clear, 0.5 gram of 200-400 mesh Dowex 50 W×8 acidic ion exchanger is added and mixed well, after which it is filtered off. The solution obtained is poured onto a flat dish and given to dry. The non-liquid proton conductor membrane obtained, which is transparent with a slight rose hue, is convened into a fuel cell as described under Example 2 above.

The cell thus obtained yields an open circuit voltage of 948 mV, a current of 750 $mA/cm^2$ can be maintained at 0.082 volts, while at a current of 225 $mA/cm^2$ the voltage is 501 mV. All data were derived under ambient conditions.

EXAMPLE 6

Figure 3A:
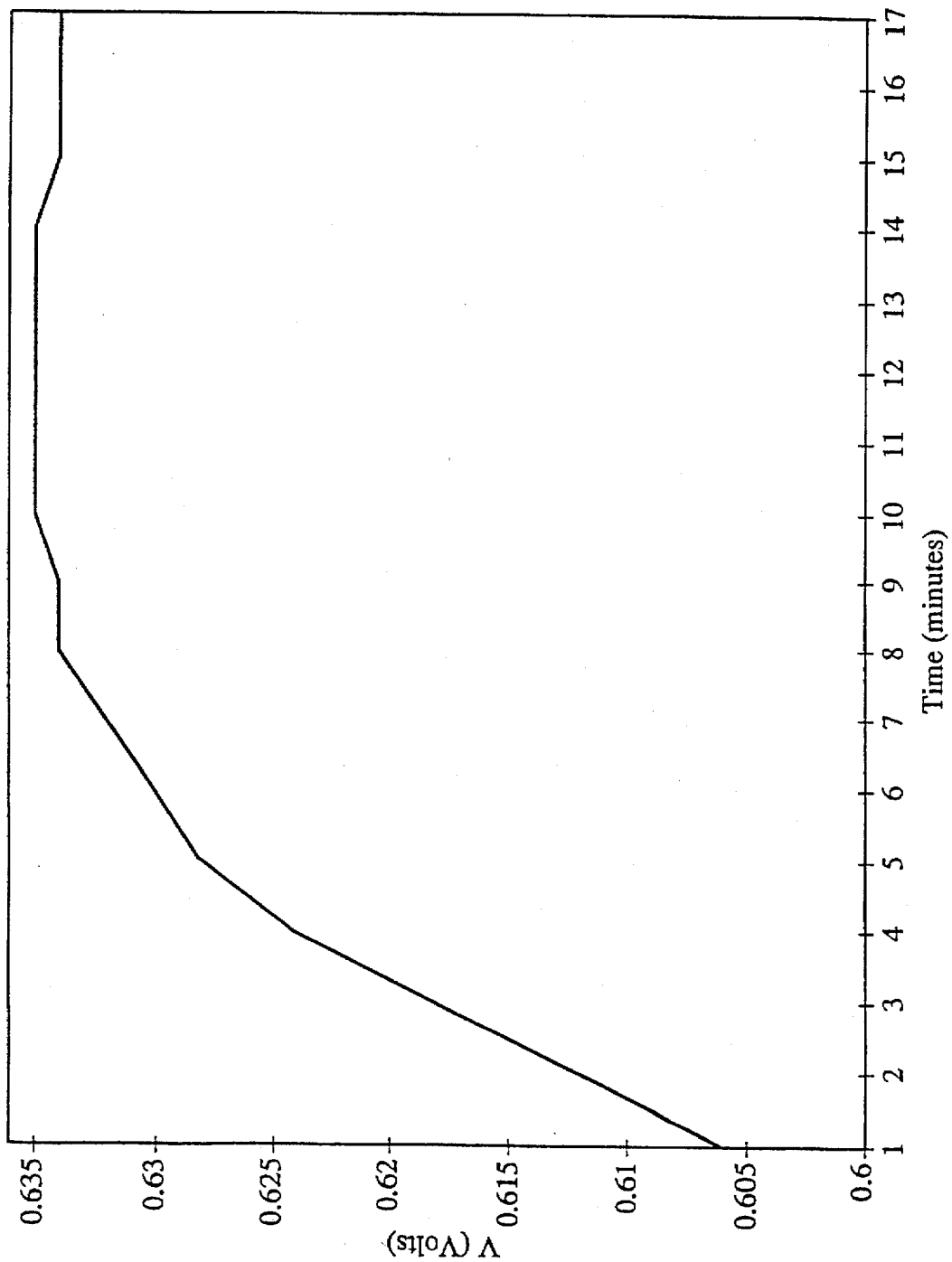
FIGS. 3a and 3b are plots demonstrating the dependency of the voltage and current, respectively, on time from operating a water producing fuel cell, constructed according to Example 5 of the present invention.
Figure 3B:
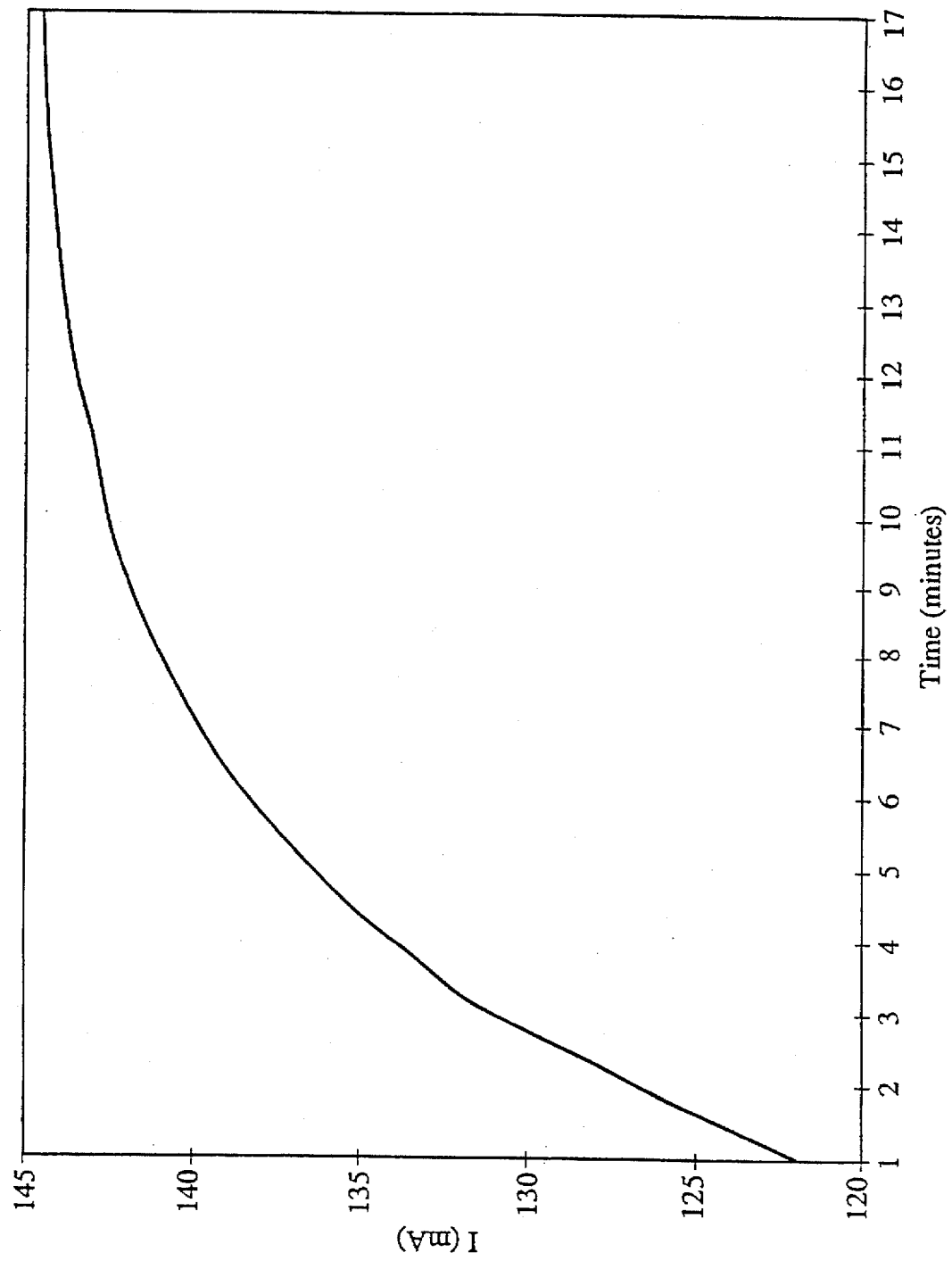

Dependency of the voltage and current on time from operating a water producing fuel cell With reference now to FIGS. 3a–b. A fuel cell was constructed as described under Example 5 above and was operated against a load of five ohms. The voltage in volts (FIG. 3a) and current in mA (FIG. 3b) were recorded as a function of time elapsed from operating the cell. At various times the swelling of the non-liquid proton conductor membrane due to water formed during the operation of the fuel cell was visually estimated. Most of the swelling occurred within Ca. ten minutes post operation of the fuel cell. Swelling and therefore contact between the membrane and the electrodes has intensified after Ca. six minutes to a degree that it was practically impossible to separate them without causing irreversible damage to the cell.

Note that the increase in voltage and currents until reaching a plateau parallels the swelling of the membrane, indicative of the formation of an improved electrical contact between the membrane and the electrodes of the fuel cell as the membrane swells.

EXAMPLE 7

Preparation of a fuel cell

The same procedure as described under Example 5 above was followed. PVA solution, polyvinylsulfonic acid sodium salt aqueous solution and Dowex powder are mixed and the Dowex filtered off. To the clear solution obtained, 50 mg of alumina powder filler are added and the mixture poured onto a flat surface and given to dry, resulting in a toughened membrane. A fuel cell as described under Example 2 above was prepared using this non-liquid proton conductor membrane. The cell yields an open circuit of 721 mV, a current of 800 mA/cm$^2$ can be maintained at 80 mV, while at a current of 225 mA/cm$^2$, the voltage is 484 mV. All data were derived under ambient conditions.

EXAMPLE 8

Preparation of a fuel cell

A fuel cell is prepared as described under example 2 above.

Using hydrogen prepared in situ as the fuel, and air as the oxidant (no auxiliary means employed), the fuel cell thus prepared has an open circuit voltage of 600 mV, and a current of 200 mA/cm$^2$ can be maintained at a voltage of 327 mV. All data were derived under ambient conditions.

Preparing hydrogen in situ may for example be by reacting a hydride compound (e.g., a metal hydride such as sodium hydride, a metal borohydride such as sodium borohydride, or a compound containing a metal hydride such as lithium aluminum hydride) or an elemental metal (e.g., sodium) with a compound that contains protons such as but not limited to water, acidic compounds, etc., in which reaction molecular hydrogen is released at ambient conditions.

While the invention has been described with respect to a limited number of embodiments, it will be appreciated that many variations, modifications and other applications of the invention may be made.

What is claimed is:

1. A method of preparing an electrochemical system selected from the group consisting of batteries, fuel cells, capacitors and electrolizers, operated at ambient temperatures, the method comprising the steps of:

(a) dissolving a matrix polymer and an acidic multimer in a first solvent to obtain a homogenous solution;

(b) pouring said homogenous solution onto a surface; and (c) evaporating said first solvent and therefore obtaining a non-liquid proton conductor membrane; and (d) interposing said non-liquid proton conductor membrane in an electrical contact between an anode plate and a cathode plate;

wherein, said matrix polymer is selected such that when said non-liquid proton conductor membrane is contacted with a second solvent, said non-liquid proton conductor membrane swells and as a result said electrical contact improves.

2. A method as in claim 1, further comprising the step of forming cross-links within said non-liquid proton conductor membrane.

* * * * *